: (12) United States Patent
Benton

(10) Patent No.: US 11,213,611 B2
(45) Date of Patent: Jan. 4, 2022

(54) CROSS-LINKED BIOPROSTHETIC TISSUE USING BIO-ORTHOGONAL BINDING PAIRS

(71) Applicant: Edwards Lifesciences Corporation, Irvine, CA (US)

(72) Inventor: Julie A. Benton, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 309 days.

(21) Appl. No.: 16/418,918

(22) Filed: May 21, 2019

(65) Prior Publication Data

US 2019/0269827 A1 Sep. 5, 2019

Related U.S. Application Data

(60) Division of application No. 15/936,097, filed on Mar. 26, 2018, now abandoned, which is a continuation of application No. 14/078,435, filed on Nov. 12, 2013, now Pat. No. 9,925,303.

(60) Provisional application No. 61/725,937, filed on Nov. 13, 2012.

(51) Int. Cl.
*A61L 27/36* (2006.01)

(52) U.S. Cl.
CPC ....... *A61L 27/3687* (2013.01); *A61L 2430/40* (2013.01)

(58) Field of Classification Search
CPC .................. A61L 2430/40; A61L 27/3687
See application file for complete search history.

(56) References Cited

U.S. PATENT DOCUMENTS

| | | | |
|---|---|---|---|
| 7,375,234 | B2 | 5/2008 | Sharpless et al. |
| 9,925,303 | B2 | 3/2018 | Benton |
| 2002/0081564 | A1 | 6/2002 | Levy et al. |
| 2005/0244460 | A1 | 11/2005 | Alferiev et al. |
| 2006/0193885 | A1 | 8/2006 | Neethling et al. |
| 2010/0196985 | A1 | 8/2010 | Hotchkiss et al. |
| 2010/0217287 | A1 | 8/2010 | Ladet et al. |
| 2011/0105496 | A1 | 5/2011 | Gamber et al. |
| 2011/0177150 | A1 | 7/2011 | Pathak et al. |
| 2012/0027814 | A1 | 2/2012 | Ladet |
| 2012/0179193 | A1 | 7/2012 | Cohn et al. |
| 2014/0302001 | A1 | 10/2014 | Do |

FOREIGN PATENT DOCUMENTS

| | | |
|---|---|---|
| WO | 2006026325 A2 | 3/2006 |
| WO | 2006110228 A2 | 10/2006 |
| WO | 2008088839 A2 | 7/2008 |
| WO | 2010100108 A1 | 9/2010 |
| WO | 2012067375 A2 | 5/2012 |
| WO | 2012068251 A2 | 5/2012 |

OTHER PUBLICATIONS

Baskin et al. Proc. Nat'l. Acad. Sci. (2007) 104(43): 16793-16797 (Year: 2007).*
Agard, N.J., et al., "A Strain-Promoted [3+2] Azide-Alkyne Cycloaddition for Covalent Modification of Biomolecules in Living Systems," JACS 126, 15046-15047, 2004.
Baskin, J.M., et al., "Bioorthogonal Click Chemistry: Covalent Labeling in Living Systems," QSAR & Combinatorial Science 26, 1211-1219, 2007.
Kolb, H.C., et al., "Click chemistry: Diverse chemical function from a few good reactions," Angewandte Chernie-International Edition 40, 2004-2021, 2001.
Rostovtsev, V.V., et al., "A stepwise Huisgen cycloaddition process: Copper(I)-catalyzed regioselective 'litigation' of azides and terminal alkynes," Angewandte Chernie-Internation Edition 41, 2596-2599, 2002.
Vila et al., "Chem. Res. Toxic" (2008) 21:432-444 (Year: 2008).
"Sigrist Methods in Enzymol," (1982) 88 (Biomembranes, Pt. 1): 207-213 (Year: 1982).
Kulbokaite et al., "Reactive and Functional Polymers," (2009) 69: 771-778 (Year: 2009).
Definition of Crosslink Downloaded from medical-dictionary.thefreedictionary.com.crosslink on May 28, 2015 (Year: 2015).
Goddard-Borger et al. Organic Lett. (2007) 9(19): 3797-3800 (Year: 2007).
Borcard et al., Bioconjugate Chem. (2011) 22: 1422-1432; published online Jun. 13, 2011 (Year: 2011).
Mahmoud et al. Biomaterials (2011; published online Feb. 2011) 32: 3712-3720 (Year: 2011).

* cited by examiner

*Primary Examiner* — Susan M Hanley
(74) *Attorney, Agent, or Firm* — Darren M. Franklin; Michelle C. Kim; Sheppard, Mullin, Richter and Hampton LLP

(57) ABSTRACT

Methods for treating a bioprosthetic tissue and treated bioprosthetic tissue are described. The methods comprise contacting the biological tissue with an anchor compound, the anchor compound comprising first and second functional groups. The first functional group is reactive with and couples a tissue functional group associated with the biological tissue. The second functional group is one of a bio-orthogonal binding pair. The biological tissue coupled to the anchor compound is then exposed to a linking compound. The linking compound comprises at least two functional groups, each comprising the other one of the bio-orthogonal binding pair. In a preferred embodiment, the bio-orthogonal binding pair is an azide and an acetylene. The method can be performed in the presence of a catalyst, preferably a copper catalyst. Alternatively, the method can be performed in the absence of a catalyst, wherein the acetylene is incorporated in a ring-strained cyclic compound, such as cyclooctyne.

16 Claims, 3 Drawing Sheets

CROSS-LINKED BIOPROSTHETIC TISSUE USING BIO-ORTHOGONAL BINDING PAIRS

CROSS-REFERENCE TO RELATED APPLICATIONS

This application is a divisional of U.S. patent application Ser. No. 15/936,097, filed Mar. 26, 2018, which is a continuation of U.S. patent application Ser. No. 14/078,435, filed Nov. 12, 2013, now U.S. Pat. No. 9,925,303, which claims the benefit of U.S. Provisional Patent Application No. 61/725,937, filed on Nov. 13, 2012, the contents all of which are incorporated by reference in their entireties.

FIELD OF THE INVENTION

The present invention is directed to methods for treating bioprosthetic tissue for implantation in a patient and, more particularly, to methods for cross-linking bioprosthetic tissue using bio-orthogonal binding pairs.

BACKGROUND

Significant challenges are presented by the use of non-autologous tissue in bioprosthetic implants. Chief among the challenges are immunological rejection and/or calcification of the bioprosthetic implant which, in turn, results in the undesirable degradation and stiffening of the tissue. Immunological rejection and calcification are particularly problematic for bioprosthetic heart valves, as calcification of these leaflets after implantation will adversely affect the leaflets' ability to maintain the required one-way flow of blood, i.e., prevent undesirable leaking or regurgitation of blood.

Glutaraldehyde has long been the reagent of choice for cross-linking biological tissues and, more particularly, for cross-linking pericardial tissue used for heart valves. Glutaraldehyde chemically modifies and cross-links collagen to render the biological tissue immunologically acceptable in the human host and stabilize the tissue. While glutaraldehyde remains the preferred cross-linking reagent, it is not without its disadvantages. Indeed, glutaraldehyde has been reported to accelerate the calcification process, which is the main cause of long-term failure in glutaraldehyde-fixed pericardial valves. Furthermore, as glutaraldehyde is cytotoxic and prevents host cell attachment, migration and proliferation, it hinders the ability of treated tissue to regenerate in vivo. Glutaraldehyde also has a tendency to polymerize and to produce undesired side reactions. The types of reactions that are implicated by glutaraldehyde are often difficult to control.

What is therefore needed are strategies that can be used in place of or in conjunction with glutaraldehyde fixation that mitigate some of the disadvantages of glutaraldehyde-treated bioprosthetic tissue.

BRIEF SUMMARY

The preferred embodiments described herein are directed to methods for treating biological tissue for use in connection with an implantable bioprosthesis.

In one preferred embodiment, a method for cross-linking biological tissue is described. The method comprises contacting the biological tissue with an anchor compound comprising first and second functional groups. The first functional group couples a tissue functional group associated with the biological tissue and the second functional group is one of a bio-orthogonal binding pair. The biological tissue is then exposed to a linking compound comprising at least two functional groups. The two functional groups each comprise the other one of the bio-orthogonal binding pair.

In accordance with a first aspect, the bio-orthogonal binding pair comprises an azide and an acetylene.

In accordance with a second aspect, the exposing is performed in the presence of a catalyst. The catalyst can be a copper, a ruthenium, a silver, salts of copper, ruthenium or silver, or derivatives of copper, ruthenium or silver. In a preferred embodiment, the catalyst is copper, a copper salt or derivatives of copper.

In accordance with a third aspect, the method further comprises rinsing the biological tissue after exposing the biological tissue with the linking compound. The rinsing can be performed using an aqueous, non-aqueous or anhydrous solution. Aqueous solutions include a saline solution, preferably a buffered saline solution, such as a phosphate-buffered saline solution. Aqueous, non-aqueous or anhydrous solutions include glycerol solutions, polyethylene glycol (PEG) solutions, and ketone solutions, such as acetones.

The term "non-aqueous," as it refers to a solution, is understood to mean a solution in which less than 50% by weight of the solution system is water. Thus, a non-aqueous solution does not exclude the presence of water, either as an impurity or in amounts less than 50% by weight.

In accordance with a fourth aspect, the acetylene is incorporated in a cyclic compound having a ring strain. In a preferred embodiment, the cyclic compound is a cyclooctyne. The cyclooctyne can comprise one or more electron-withdrawing groups, preferably a halogen and most preferably a fluorine.

In accordance with a fifth aspect, the exposing is performed in the absence of a catalyst.

In accordance with a sixth aspect, the tissue functional group is one or more selected from the group consisting of an amine, a hydroxyl, a sulfhydryl, a carbonyl, and a carboxylic acid. The tissue functional group is preferably an amine and the first functional group of the anchor compound is an aldehyde.

In accordance with a seventh aspect, the first functional group of the anchor compound is selected from the group consisting of an isothiocyanate, an isocyanate, a sulfonyl chloride, an aldehyde, a carbodiimide, an acyl azide, an anhydride, a fluorobenzene, a carbonate, an N-Hydroxysuccinimides (NHS), an NHS ester, an imidoester, an epoxide, a fluorophenyl ester, an amine, a carboxylic acid, and an alcohol.

In accordance with an eighth aspect, the anchor compound is one or a combination of an imidazole-1-sulfonyl azide and trifluoromethanesulfonyl azide.

In accordance with a ninth aspect, either one or both of the anchor and the linking compounds comprises a spacer.

In accordance with a tenth aspect, the spacer does not comprise functional groups that are reactive with the biological tissue, with the tissue functional group or any one of the bio-orthogonal binding pair.

In accordance with an eleventh aspect, the linking compound comprises the spacer. The spacer can be one or a combination selected from branched or straight-chain saturated or unsaturated hydrocarbons and a polymer. The spacer can also or additionally comprise one or a combination of a bioactive and a biodegradable group. The biodegradable group can be a disulfide.

In another embodiment, a cross-linked bioprosthetic tissue produced in accordance with any one of the foregoing methods is provided.

In accordance with a first aspect, the cross-linked bioprosthetic tissue is not treated with glutaraldehyde, formaldehyde, or other aldehyde-containing crosslinker.

In accordance with a second aspect, the cross-linked bioprosthetic tissue is provided in a sealed package that does not contain a liquid preservative solution in contact with the tissue.

Other objects, features and advantages of the described preferred embodiments will become apparent to those skilled in the art from the following detailed description. It is to be understood, however, that the detailed description and specific examples, while indicating preferred embodiments of the present disclosure, are given by way of illustration and not limitation. Many changes and modifications within the scope of the present disclosure can be made without departing from the spirit thereof, and the disclosure includes all such modifications.

BRIEF DESCRIPTION OF THE DRAWINGS

Illustrative embodiments of the present disclosure are described herein with reference to the accompanying drawings, in which.

DETAILED DESCRIPTION OF THE PREFERRED EMBODIMENTS

Figure 1:
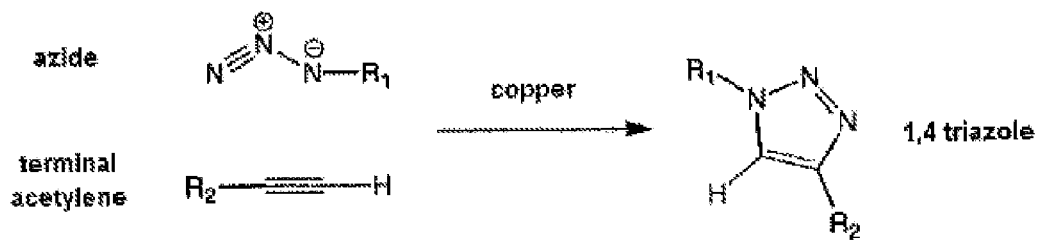
FIG. 1 depicts the copper-catalyzed azide-alkyne cycloaddition reaction scheme.

Specific, non-limiting embodiments of the methods for cross-linking bioprosthetic tissue will now be described with reference to the drawings. It should be understood that such embodiments are by way of example only and merely illustrative of but a small number of embodiments within the scope of the present disclosure. Various changes and modifications obvious to one skilled in the art to which the present disclosure pertains are deemed to be within the spirit, scope and contemplation of the present disclosure as further defined in the appended claims.

The preferred embodiments described herein are directed to methods for treating biological tissue for use in connection with an implantable bioprosthesis. Because biological tissues used for implantable bioprostheses originate from non-autologous sources, the biological tissue must be treated prior to implantation to maintain a sufficient degree of mechanical strength and dimensional stability. At the same time, the biological tissue must also be treated to reduce its antigenicity in the patient and to reduce actual and potential binding sites for calcium.

Glutaraldehyde has long been the reagent of choice for cross-linking and sterilizing biological tissues for use in prosthetic heart valves. The use of glutaraldehyde, however, has many significant disadvantages. Because of its tendency to polymerize in solution, glutaraldehyde fixation often results in the generation of aldehydes groups associated with the fixed tissue. Additionally, glutaraldehyde reacts with the free amines in the tissue to generate labile Schiff bases. Both aldehydes and Schiff bases represent potential calcium binding sites that may lead to calcification. Additionally, glutaraldehyde cross-linking affords limited opportunities to tailor the properties of the cross-linked tissue after fixation and provides little or no synthetic handles for the rational design of a cross-linked network. Moreover, because glutaraldehyde is cytotoxic, it prevents the desired cellular in-growth and integration of the implanted and glutaraldehyde-treated bioprosthetic tissue.

The present disclosure describes alternative methods for cross-linking biological tissue using an anchor compound and a difunctional linking compound, the anchor and difunctional linking compounds each comprising complementary ones of a bio-orthogonal binding pair. The reaction between the bio-orthogonal binding pair has certain advantages over glutaraldehyde-based fixation. One advantage is that the reaction between the bio-orthogonal binding pair is highly specific to one another, thereby reducing or even eliminating the possibility of undesired side reactions between any one of the bio-orthogonal binding pair and tissue functional groups present in or native to biological tissue.

As used herein, "bio-orthogonal binding pair" refers to a pair of functional groups which react with and couple one another. The reaction and coupling between complementary ones of the bio-orthogonal binding pair is mutually exclusive such that each one of the bio-orthogonal binding pair does not react with any tissue functional groups or with any functional groups found inside living systems.

As used herein, "tissue functional groups" refer to functional groups which are native to biological tissue and, more particularly, in collagenous tissue, such as, for example, cardiac valves, blood vessels, skin, dura mater, pericardium, small intestinal submucosa ("SIS tissue"), ligaments and tendons. Exemplary tissue functional groups include amines, hydroxyls, sulfhydryls, aldehydes, and carboxylic acids.

In a preferred embodiment, the bio-orthogonal binding pair comprises an azide and an acetylene. It is understood that the azide and acetylene groups of the bio-orthogonal binding pair can be present as either a terminal or an internal group within an anchor compound or a linking compound used in accordance with the method. While the reaction of the bio-orthogonal binding pair itself is specific to one another, one or both of the anchor compound and the linking compound can comprise additional functional groups, such as those which react with tissue functional groups which can be reactive with other functional groups, such as tissue functional groups. However, it is understood that the additional functional groups of the first or linking compound are not reactive with any one of the bio-orthogonal binding pair.

The reaction between the bio-orthogonal binding pair can take place either in the presence or absence of a catalyst. FIG. 1 depicts a copper-catalyzed reaction between an exemplary bio-orthogonal binding pair comprising an azide and an alkyne functional group. As shown in FIG. 1, the reaction of an azide with an acetylene results in a cyclic 1,4-disubstituted [1,2,3]-triazole. The inclusion of a copper catalyst permits this reaction to take place in an aqueous solution and at room temperature. In a preferred embodiment, the copper is a copper salt or a copper derivative.

In the context of cross-linking biological tissue, the biological tissue is contacted with an anchor compound comprising one of the bio-orthogonal binding pairs. In order to couple the anchor compound onto the biological tissue, the anchor compound preferably comprises a first functional group that forms a covalent bond with or otherwise couples a tissue functional group associated with the biological tissue. In one embodiment, the one of the bio-orthogonal binding pairs and the first functional group can be located on terminal ends of the anchor compound, which can be straight-chained or branched.

In a preferred embodiment, the biological tissue is not cross-linked with glutaraldehyde or any other aldehyde-containing agent. In a particularly preferred embodiment, the biological tissue is cross-linked using only the anchor and difunctional linking compounds disclosed herein, in which the anchor comprises one of the bio-orthogonal binding pair and the difunctional linking compound comprises the other one of the bio-orthogonal binding pair. In accordance with this embodiment, the first functional group of the anchor compound is not an aldehyde group. Preferably, the first functional group is also not a carboxylic acid group. In a further preferred embodiment, neither one of the anchor nor the linking compound comprises an aldehyde or a carboxylic acid group. In one embodiment, the anchor compound is one or a combination of an imidazole-1-sulfonyl azide and trifluoromethanesulfonyl azide.

Figure 4:
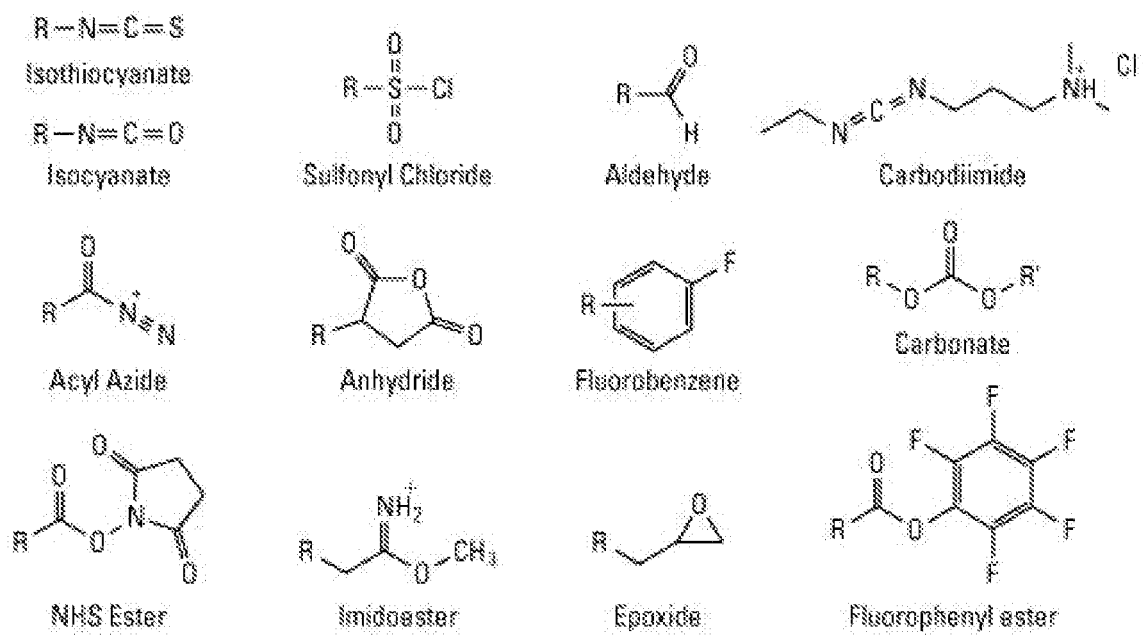
FIG. 4 depicts exemplary embodiments of functional groups which are reactive with, and thus couples with a tissue functional group associated with a biological tissue.

Examples of first functional groups include isothiocyanate, isocyanate, sulfonyl chloride, aldehydes, carbodiimides, acyl azides, anhydrides, fluorobenzenes, carbonates, N-Hydroxysuccinimides (NHS), NHS esters, imidoesters, epoxides, fluorophenyl esters and are depicted in FIG. 4. The first functional groups can also include amines, carboxylic acids and alcohols. The R represented in each of these structures can comprise one of the bio-orthogonal binding pair or a combination of a spacer and one of the bio-orthogonal binding pair.

Figure 5A:
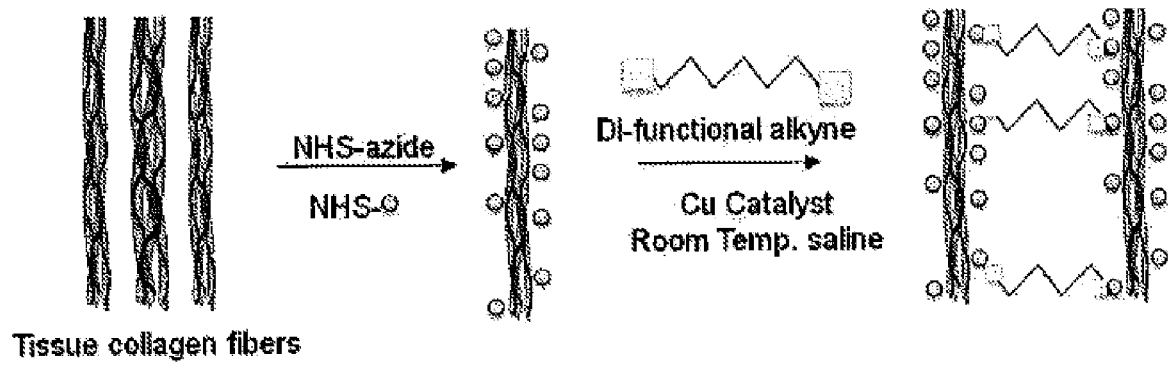
FIGS. 5A-5B depicts an exemplary method in which the anchor and linking compounds comprising the bio-orthogonal binding pair effectuates cross-links between tissue collagen fibers.
Figure 5B:
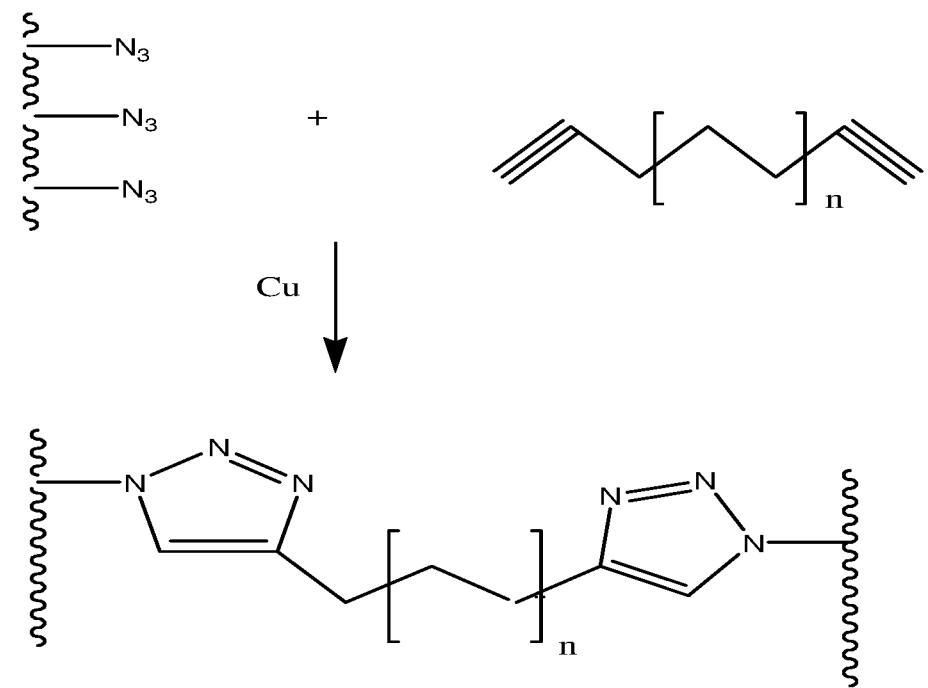

FIGS. 5A and 5B depict the mechanism of cross-linking biological tissues utilizing an anchor compound comprising one of the bio-orthogonal binding pair and a linking compound comprising the other one of the bio-orthogonal binding pair. While FIGS. 5A and 5B depict the cross-linking being performed with the anchor compound comprising the azide and the linking compound comprising the di-functional alkyne, it is understood that the cross-linking can be performed with an anchor compound comprising an alkyne and a linking compound comprising a di-functional azide. The linking compound is preferably homodifunctional so as to prevent the linking compound from polymerizing.

As shown in FIGS. 5A and 5B, the azide is coupled to the tissue collagen fibers by way of a first functional group which couples with a tissue functional group to couple the anchor compound onto the biological tissue. The biological tissue that is coupled to the anchor compound is then exposed to a linking compound comprising at least two functional groups, the two functional groups each comprising the other one of the bio-orthogonal binding pair. As depicted in FIGS. 5A and 5B, the linking compound is a di-functional alkyne, with the alkyne being located at the terminal ends of the linking compound.

Either one or both of the anchor and linking compounds can further comprise a spacer. In FIG. 5B, the di-functional alkyne is depicted as comprising an alkyl spacer having a length n. The length of the spacer can be tailored based on the desired mechanical properties for the resulting cross-linked biological tissue. For example, longer spacers can be provided to produce a more pliable or flexible cross-linked tissue, whereas shorter spacers can be provided to produce a stiffer cross-linked tissue. In a preferred embodiment, the spacer has a length of $10 \geq n \geq 3$. The spacer can be selected from one or a combination of a branched or straight-chain saturated or unsaturated hydrocarbon or a polymer, such as a polyethylene glycol (PEG). The spacer can also be one or a combination of a polymeric elastomer, such as a polyurethane, a polyisobutylene, and a polysiloxane, a polymeric carbohydrate, such as a polysaccharide, hyaluronic acid, dextran sulfate, and heparin.

The spacer can further comprise one or a combination of a bioactive or a biodegradable group. The biodegradable group can be one or a combination of disulfides, polyesters, orthoesters, polyhydroxybutyric acid, poly(glycolide), poly(lactide) and copolymers of poly(glycolide) and poly(lactide). The bioactive group can be incorporated to either promote or repress specific cell interactions within the biological tissue or between the biological tissue and the host, once implanted. The biodegradable group, such as a disulfide, can be provided on the spacer to permit the ability to partially or completely dissolve or dissociate the cross-linkages formed within the biological tissue at a desired time after implantation in the host. The ability to partially or completely dissolve or dissociate the cross-linkages can be desirable in order to permit cellular migration and in-growth such that the implanted biological tissue becomes integrated with the host on a cellular level. The spacer can further include additional functional groups which can be used to couple or tether a specific drug or imaging molecule.

It is understood that the inclusion of additional functional groups on the spacer, however, preferably does not comprise any functional groups that would be reactive with the biological tissue, the tissue functional groups or any one or both of the bio-orthogonal binding pair.

The reaction between the bio-orthogonal binding pair can be facilitated with a catalyst. Thus, the exposing of the biological tissue coupled to the anchor compound to the linking compound can be performed in the presence of a catalyst. Preferred catalysts include one or a combination of a copper-based catalyst, a ruthenium-based catalyst and a silver-based catalyst. In another preferred embodiment, the catalyst includes one or a combination of a copper salt, a ruthenium salt and a silver salt. In a further preferred embodiment, the catalyst includes one or a combination of a copper-based derivative, a ruthenium-based derivative and a silver-based derivative.

In a preferred embodiment, the catalyst is a Cu(I) catalyst. Because the Cu(I) catalyst is cytotoxic, it has the advantage of also serving as a sterilant for the cross-linked biological tissue. In embodiments where a cytotoxic catalyst is used, the method further comprises rinsing the bioprosthetic tissue after the exposing step to eliminate or reduce the levels of the cytotoxic catalyst to at or below a physiologically-acceptable limit.

In one preferred embodiment, the rinsing can be performed using an aqueous, non-aqueous or anhydrous solutions. Aqueous solutions include a saline solution, preferably a buffered saline solution, such as a phosphate-buffered saline solution. Aqueous, non-aqueous or anhydrous solutions include glycerol solutions, polyethylene glycol (PEG) solutions, and ketone solutions, such as acetones. Treatment with certain aqueous, non-aqueous or anhydrous solutions, such as those involving glycerol, permits the bioprosthetic tissue to be stored dry, i.e., in a manner that the tissue is not in contact with a liquid preservative solution. In an alternative embodiment, the cross-linking of the biological tissue can be performed in the absence of a catalyst. In this embodiment, the bio-orthogonal binding pair can comprise an azide and a cycloalkyne. The cycloalkyne is characterized as having sufficient ring-strain to drive the cycloaddition reaction between the azide and the cycloalkyne at room temperature and without the need for a catalyst to drive the forward reaction.

In a preferred embodiment, the cycloalkyne has a ring strain of greater than 5 kcal/mol, more preferably greater than 10 kcal/mol and most preferably greater than 15 kcal/mol.

In another preferred embodiment, the cycloalkyne comprises one or more electron-withdrawing substituent. The one or more electron-withdrawing substituent preferably comprise one or more halogens, most preferably fluorine. In a particularly preferred embodiment, the cycloalkyne is a mono- or di-fluorinated cyclooctyne in which the electron-withdrawing fluorine substituents are located at the propargylic position.

Figure 2:
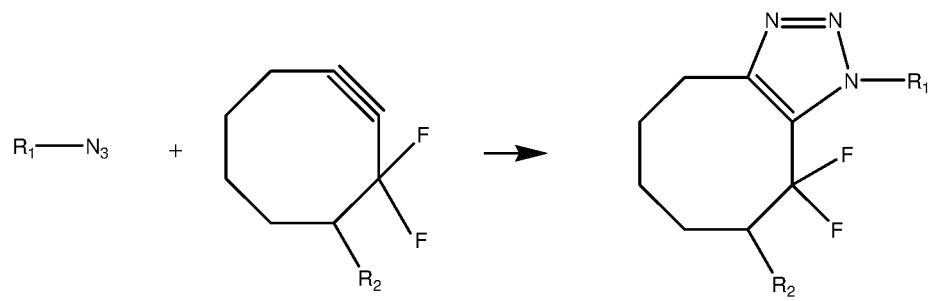
FIG. 2 depicts the azide-cyclooctyne cycloaddition reaction scheme.
Figure 3:
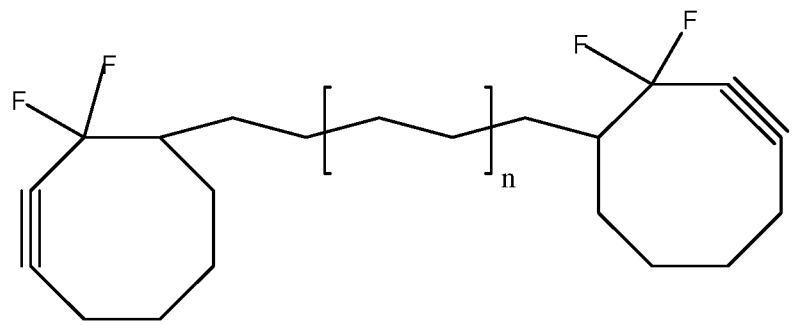
FIG. 3 depicts an embodiment of a ring-strained linking compound.

FIG. 2 depicts the azide-di-fluorinated cyclooctyne cycloaddition reaction scheme in which the electron-withdrawing fluorine substituents are located at the propargylic position. FIG. 6 further depicts a linking compound comprising two di-fluorinated cyclooctyne groups at terminal ends of an alkyl or polymer spacer having n length.

After treatment of the tissue with the anchor and linking compounds comprising the bio-orthogonal binding pair, the tissue can be further treated to cap functional groups which play a role in tissue calcification. Such functional groups can include aldehyde and carboxylic acid groups on the native tissue or which result from treating or exposing the tissue with glutaraldehyde, formaldehyde or other aldehyde-containing compounds.

Thus, in one preferred embodiment, particularly in embodiments where the tissue is also treated with glutaraldehyde, formaldehyde and other aldehyde-containing compounds, the process can further comprise a treatment with a capping and a reducing agent following the crosslinking of the tissue using the anchor and difunctional linking compounds described above.

Insofar as the tissue may comprise residual aldehyde groups, the tissue can be subjected to a capping process by contacting the tissue with a capping agent, such as ethanolamine, and a reducing agent, such as sodium borohydride. Exemplary capping and reducing agents and processes are described in U.S. Pat. No. 7,972,376, the entire contents of which are incorporated by reference, as if fully set forth herein.

Alternatively, tissue aldehydes can also be oxidized to carboxylic acids and the carboxylic acids can be reacted with alcohols or amines.

In yet further embodiments, tissue functional groups can be reacted with various nucleophiles and/or electrophiles in the presence of an appropriate catalyst, as described in U.S. patent application Ser. No. 14/074,379, filed Nov. 7, 2013, the entire contents of which are incorporated herein by reference, as if fully set forth herein.

The bioprosthetic tissue can further undergo treatment with anhydrous, non-aqueous or aqueous glycerol solutions to substantially, if not completely, dehydrate the bioprosthetic tissue for dry storage.

In a preferred embodiment, the anhydrous or non-aqueous solution comprises glycerol and, more preferably, a solution of 75 wt % glycerol and 25 wt % ethanol, and the bioprosthetic tissue is soaked in the glycerol solution for at least one hour. The bioprosthetic tissue is then removed and placed in a clean hood to allow removal of excess solution.

In a preferred embodiment, the anhydrous or non-aqueous solution is a solution of glycerol and a $C_1$-$C_3$ alcohol, wherein the treatment solution comprises 60-95% by volume glycerol. Suitable treatment for the biological tissues are described in U.S. Pat. No. 8,007,992, issued Aug. 30, 2011, to Edwards Lifesciences Corp., the entire contents of which are incorporated herein by reference as if fully set forth herein.

In another preferred embodiment, an aqueous glycerol solution can be used to at least partially dehydrate the tissue, as described in U.S. Pat. No. 6,534,004, issued Mar. 18, 2003, issued to The Cleveland Clinic Foundation, the entire contents of which are incorporated herein by reference in its entirety as if fully set forth herein.

The terms "dry" or "dehydrated," as used herein, is understood to include residual treatment solution or moisture or humidity from the ambient environment following treatment with the anhydrous, non-aqueous or aqueous glycerol solutions.

The dehydrated bioprosthetic tissue is provided in a sealed package, preferably in a double sterile barrier packaging consisting of a rigid tray (PETG) with a Tyvek lid. The sealed package preferably does not contain a liquid preservative solution in contact with the tissue. The package is sealed in a clean room, and sterilized in 100% ethylene oxide.

While the present disclosure describes specific embodiments of bio-orthogonal binding pairs, it is understood that it is not so limited and that the disclosure encompasses any pair of functional groups which engage in a mutually exclusive reaction and coupling with one another. Thus, it is to be understood that the detailed description and specific examples, while indicating preferred embodiments of the present invention, are given by way of illustration and not limitation. Many changes and modifications within the scope of the present invention can be made without departing from the spirit thereof, and the disclosure includes all such modifications.

What is claimed is:

1. A cross-linked bioprosthetic tissue comprising:
   a biological tissue comprising one or more tissue functional groups;
   a plurality of anchor compounds, each of the plurality of the anchor compounds comprising a first functional group and a second functional group, the first functional group being coupled to one of the one or more tissue functional groups of the biological tissue and the second functional group being one of a bio-orthogonal binding pair; and
   a plurality of linking compounds, each of the plurality of linking compounds comprising at least two functional groups, the at least two functional groups comprising the other one of the bio-orthogonal binding pair;
   wherein each one of the at least two functional groups of each linking compound is coupled to the second functional group of one of the plurality of anchor compounds to form cross-linkages within the biological tissue;
   wherein the bio-orthogonal binding pair comprises an azide and an acetylene; and
   wherein the first functional group of each of the plurality of anchor compounds is selected from the group consisting of: a carbodiimide, a fluorobenzene, and a fluorophenyl ester.

2. The cross-linked bioprosthetic tissue of claim 1, wherein the acetylene is incorporated in a cycling compound having ring strain.

3. The cross-linked bioprosthetic tissue of claim 2, wherein the acetylene is a cyclooctyne comprising one or more electron-withdrawing groups.

4. The cross-linked bioprosthetic tissue of claim 3, wherein at least one of the one or more electron-withdrawing groups is a halogen.

5. The cross-linked bioprosthetic tissue of claim 4, wherein the halogen is fluorine.

6. The cross-linked bioprosthetic tissue of claim 1, wherein each of the one or more tissue functional groups is selected from the group consisting of: an amine, a hydroxyl, a sulfydryl, a carbonyl, and a carboxylic acid.

7. The cross-linked bioprosthetic tissue of claim 1, wherein either one or both of the plurality of anchor compounds and the plurality of linking compounds comprises a spacer.

8. The cross-linked bioprosthetic tissue of claim 7, wherein the spacer does not comprise functional groups that are reactive with the biological tissue, the one or more tissue functional groups, or any of the bio-orthogonal binding pair.

9. The cross-linked bioprosthetic tissue of claim 7, wherein:
   at least one of the plurality of linking compounds comprises the spacer; and
   the spacer comprises at least one of a polysaccharide and a dexan sulfate.

10. The cross-linked bioprosthetic tissue of claim 7, wherein the spacer is selected from the group consisting of: branched or straight-chain saturated and unsaturated hydrocarbons.

11. The cross-linked bioprosthetic tissue of claim 7, wherein the spacer comprises one or a combination of a bioactive and a biodegradable group.

12. The cross-linked bioprosthetic tissue of claim 11, wherein:
   the spacer comprises the biodegradable group; and
   the biodegradable group is a disulfide.

13. The cross-linked bioprosthetic tissue of claim 1, wherein the azide is present as an internal group within each of the plurality of anchor compounds and/or the acetylene is present as an internal group within the linking compound.

14. A cross-linked bioprosthetic tissue comprising:
   a biological tissue comprising one or more tissue functional groups;
   a plurality of anchor compounds, each of the plurality of the anchor compounds comprising a first functional group and a second functional group, the first functional group being coupled to one of the one or more tissue functional groups of the biological tissue and the second functional group being one of a bio-orthogonal binding pair; and
   a plurality of linking compounds, each of the plurality of linking compounds comprising at least two functional groups, the at least two functional groups comprising the other one of the bio-orthogonal binding pair;
   wherein each one of the at least two functional groups of each linking compound is coupled to the second functional group of one of the plurality of anchor compounds to form cross-linkages within the biological tissue;
   wherein the bio-orthogonal binding pair comprises an azide and an acetylene;
   wherein at least one of the plurality of anchor compounds comprises a spacer;
   wherein the spacer comprises a biodegradable group; and
   wherein the first functional group of each of the plurality of anchor compounds is selected from the group consisting of: an isothiocyanate, an isocyanate, a sulfonyl chloride, an aldehyde, a carbodiimide, an acyl azide, an anhydride, a fluorobenzene, a carbonate, and a fluorophenyl ester.

15. The cross-linked bioprosthetic tissue of claim 14, wherein:
   either one or both of the plurality of anchor compounds and plurality of linking compounds comprises a spacer; and
   the spacer comprises at least one functional group coupled to an imaging molecule.

16. The cross-linked bioprosthetic tissue of claim 14, wherein each of the plurality of anchor compounds and each of the plurality of linking compounds comprises a spacer.

* * * * *